Figure 1:
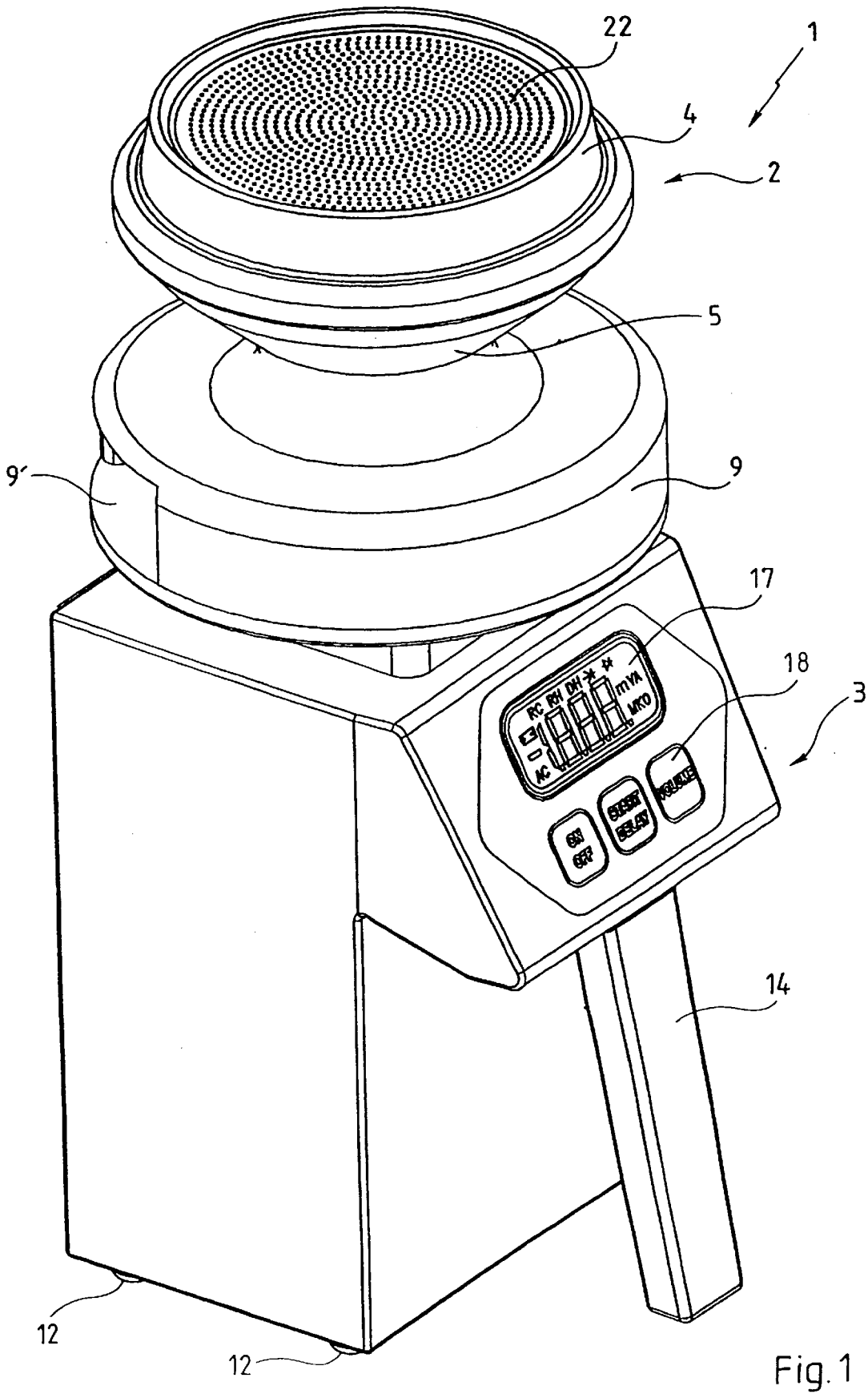
Figure 2:
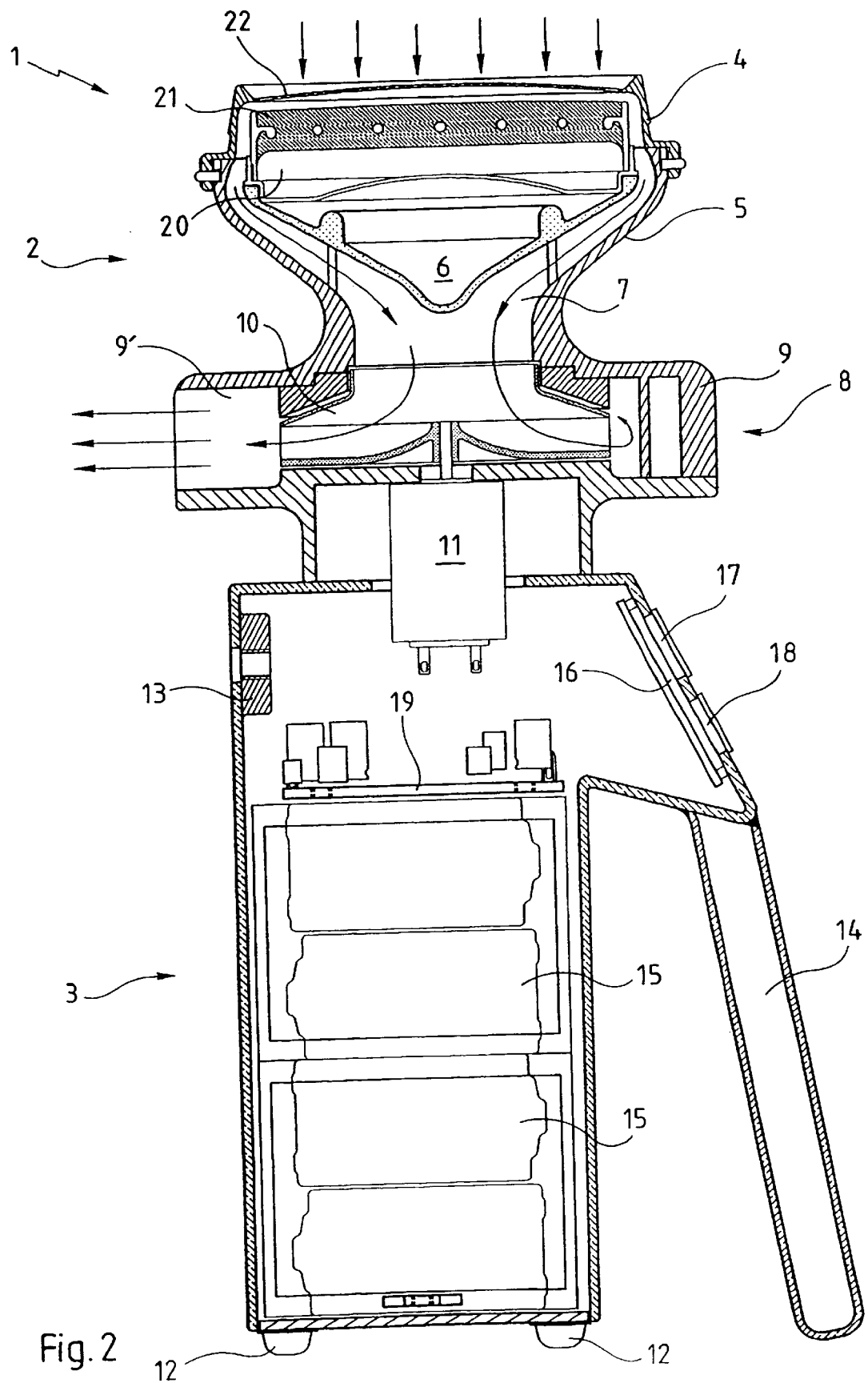
Figure 3:
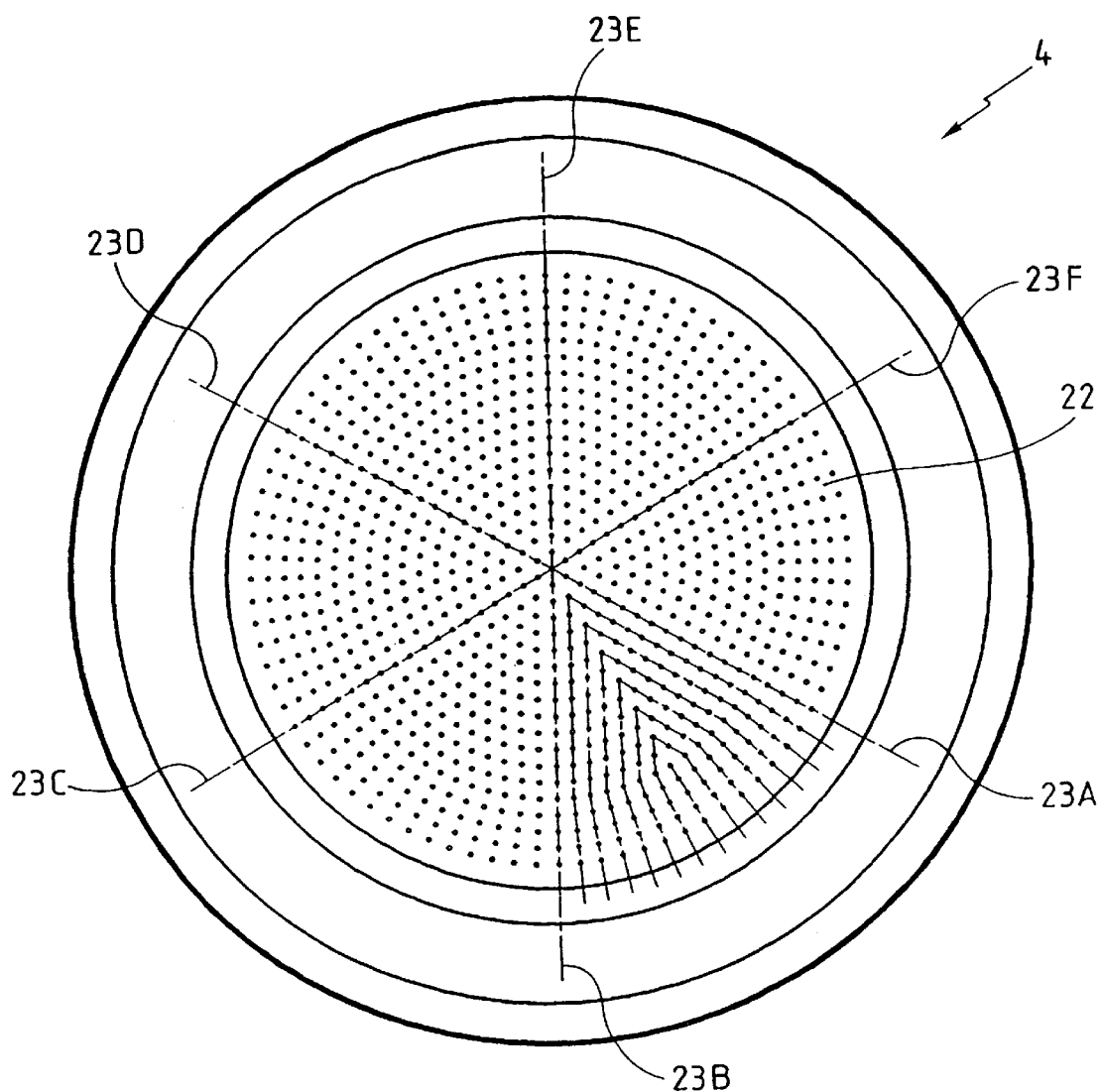
Figure 4:
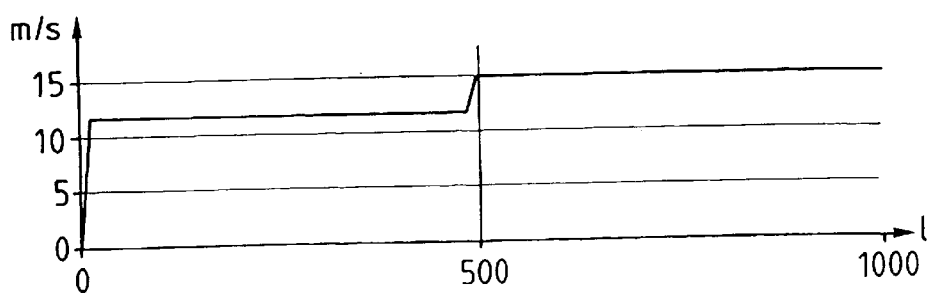

United States Patent [19]
Lemonnier

[11] Patent Number: 6,094,997
[45] Date of Patent: Aug. 1, 2000

[54] SAMPLING APPARATUS FOR THE MICROBIOLOGICAL ANALYSIS OF AIR

[75] Inventor: Jean Lemonnier, Paris, France

[73] Assignee: Millipore S.A., Mohlshein, France

[21] Appl. No.: 09/310,843

[22] Filed: May 12, 1999

[30] Foreign Application Priority Data

Jun. 10, 1998 [FR] France .................................. 98 07299

[51] Int. Cl.⁷ .................................................. G01N 1/00
[52] U.S. Cl. ....................................................... 73/863.22
[58] Field of Search ........................... 73/863.21, 863.22, 73/28.04, 28.05; 435/309.1

[56] References Cited

U.S. PATENT DOCUMENTS 3,922,905  12/1975  Roth ............................................ 73/28

FOREIGN PATENT DOCUMENTS 2 732 692  10/1996  France .
2 224 118   4/1990  United Kingdom .

*Primary Examiner*—Robert Raevis
*Attorney, Agent, or Firm*—John Dana Hubbard, Esq.; Timothy J. King, Esq.

[57] ABSTRACT

This apparatus has a sieve (4) with a wall (22) perforated with a multitude of holes, means (4, 5) for holding a removable receptacle (20) containing a layer of growth media (21) and means (7, 8) for sucking in air at the periphery of the receptacle (20) in order to cause to enter the apparatus (1), through holes in the wall (22), air which strikes the layer of growth media (21), the latter and the wall (22) being shaped so that their separation increases from their periphery towards their center.

20 Claims, 3 Drawing Sheets

SAMPLING APPARATUS FOR THE MICROBIOLOGICAL ANALYSIS OF AIR

The invention relates to the microbiological analysis of air. More particularly, it relates to a device for conducting the microbiological analysis of air.

BACKGROUND OF THE INVENTION

It is known that, in order to effect a microbiological analysis of air, use is generally made of a sampling apparatus for depositing microorganisms, such as bacteria, yeasts or molds, present in an air sample, on a layer of growth media, such as growth media, in a receptacle, and then this receptacle is incubated at the required temperature and for the required length of time to enable the deposited microorganisms to develop in the form of colonies visible to the naked eye, so that they can be counted and identified.

SUMMARY OF THE INVENTION

The invention aims to make it possible to perform the operation of depositing microorganisms on the layer of growth media both rapidly and under conditions such that the colonies which are visible after incubation faithfully reflect the microorganism population of the sample being checked.

To this end, it is proposed a sampling apparatus for the microbiological analysis of air, having a sieve with a wall perforated with a multitude of holes, a means for holding a removable receptacle containing a layer of growth media with a contour similar to that of the said perforated wall in a predetermined position in which the said layer of growth media is disposed opposite the said perforated wall and concentrically with it, and a means for sucking air at the periphery of the said receptacle held in the said predetermined position, in order to cause the air to enter the said apparatus, through the said holes, where it strikes the said layer of growth media; characterized in that the said perforated wall of the sieve and the said layer of growth media in the receptacle are shaped so that their separation increases from their periphery to their center.

This increase in separation enables the air to enter the apparatus more uniformly, and therefore more usefully, in particular in the central area of the perforated wall.

As a matter of fact, whereas in the prior apparatus where the perforated wall and the layer of growth media are parallel, the ratio between a surface of radius r of the perforated wall and the peripheral section through which the air which has entered through this surface can be discharged, varies exactly with the radius r (the ratio is equal to er/2 where e is the constant separation between the layer of growth media and the perforated wall), in the apparatus according to the present invention, the increase in separation from the periphery towards the center makes it possible to have a cross section of flow of air which is everywhere sufficiently great with respect to the surface through which the air has entered in order to afford correct discharge of the air, including in the central area of the perforated wall.

In addition, the increase in separation from the periphery to the center has the effect that the air jets created by the perforated wall have to travel, between the latter and the growth media, a distance which is the greater, the smaller the volume of air to be discharged, and is therefore the greater, the easier it is for the air jets to reach the growth media across the air flow currently being discharged towards the periphery of the receptacle.

The increase in separation thus makes it possible to provide, in the perforated wall, a large number of holes capable of being useful, that is to say holes through which an air flow can be established, coming to strike the growth media in the form of a jet having a speed which is sufficiently high for any microorganism present in the air flow to be fixed to the layer of growth media by impaction and sufficiently low for the microorganism to remain revivable.

By virtue of this possibility of disposing a large number of useful holes in the perforated wall, for example 1000 useful holes whilst in the prior apparatus the perforated wall of the sieve has at a maximum 400 holes, the microorganisms can be deposited on the layer of growth media under conditions which are more favorable to accuracy of the analysis, and the sample can be taken more rapidly.

This is because a higher number of useful holes makes it possible to have a greater total surface through which the air enters through the perforated wall, and consequently to have a higher sampling rate (for example 140 to 180 l/mm, which makes it possible to sample 1 $m^3$ in less than 7 minutes) whilst the speed at which the air jets strike the layer of growth media is similar to that of the prior apparatus, that is to say it remains within limits enabling the jets to be useful.

The conditions of deposition of the microorganisms are more favorable since having more useful holes on the one hand enables the growth media to retain more microorganisms and on the other hand avoids having several microorganisms being impacted at the same place on the layer of growth media, which would give rise to a false assessment of the microbiological population present in the air sample since the colonies of the respective microorganisms impacted at the same point would overlap and would then be counted as the colony of a single microorganism.

The growth media is capable of retaining more microorganisms since the volume of air passing through each hole is smaller (on average, 1 liter per hole with 1000 holes instead of 2.5 liters per hole with 400 holes for a sample of 1 $m^3$ of air) so that each area of the growth media struck by an air jet (an area where a small crater forms on the growth media) is less dried by the air flow, and therefore retains better adhesion and hardness properties, and consequently better capability of retaining the microorganisms over the sampling period.

The reduction in risk of overlapping of the colonies is achieved by virtue of this decrease in the volume passing through each hole, since the lower the volume of air brought in by a jet striking the growth media, the lower the risk that there will be several microorganisms in this volume, and is also achieved by virtue of the uniformity of exposure of the growth media to the sample air, that is to say to the fact that approximately the same flow rate, and therefore the same volume of air, is caused to pass through each hole, which avoids certain areas of the growth media being struck by a higher volume of sample air than other areas, and therefore they have a higher risk of receiving several microorganisms at the same place (in the same crater).

According to preferred features, the said perforated wall of the sieve is concave on the side which faces the said layer of growth media whilst the latter is flat on the side which faces the perforated wall of the sieve.

The variation in separation between the layer of growth media and the perforated wall is thus particularly simple to implement with greater precision, favorable to the reproducibility of the measurements.

Preferably, the said perforated wall of the sieve is in the form of a spherical cap.

The tests carried out by the inventor in fact showed that excellent results could be obtained with such a shape in a portion of a sphere, such as an arc.

According to other preferred features, the said holes in the perforated wall are solely disposed in concentric circles as well as, for a plurality of said circles, consecutive as from the center, in a plurality of identical series of substantially parallel chevrons, whose apex is turned towards the center, each said series of chevrons being delimited externally by a chevron formed by two radii.

The perforated wall is thus subdivided into a certain number of identical circular sectors having, between the alignments of holes, channels discharging air towards the periphery, the number of these channels increasing from the center towards the periphery of the perforated wall.

Thus, at least in the central region of the perforated wall, the co-existence between the air entering the apparatus in the form of jets and the air being discharged peripherally takes place with a minimum of mutual interference, the air jets forming kinds of columns aligned in rows delimiting paths for the discharge of air to the periphery without obstacle, the air in particular being able to circulate in these paths without having to pass round air jets situated in the middle of a path, which is favorable to a correct discharge of the air.

It will be noted that this arrangement of the holes in the perforated wall by itself makes it possible to provide a large number of useful holes in the perforated wall, and can therefore be envisaged with a separation between the layer of growth media and the perforated wall which does not increase as disclosed above.

Preferably, for each circle of the said plurality of circles, the nth circle from the center has sn holes, s being the number of identical series of chevrons.

If for example there are six identical series of chevrons, the first circle from the center has six holes, the second circle twelve holes, and so on, whilst for each series of chevrons the outermost chevron is formed by two radii, the following consecutive chevron is parallel to these radii and has its apex on the second circle, the second chevron has its apex on the fourth circle, and so on.

With these features, excellent uniformity of distribution of the holes on the perforated walls is obtained.

Preferably, the said plurality of identical series of chevrons is formed by six said series.

This figure constitutes an excellent compromise where the number of holes and the number of paths discharging air to the periphery are balanced.

Preferably, as from the (p+1)th consecutive circle as from the center, each circle has the same number of holes as the pth circle and each of its holes is aligned, on a radius, with a respective hole of the pth circle, p being the number of circles in the said plurality of consecutive circles.

Thus, as from the (p+1)th circle, the peripheral air discharge channels are extended simply in a radial orientation, without new channels being created.

The number of holes remains the same from one circle to another but, as these circles are in the peripheral area of the perforated wall, the lack of uniformity in the number of holes per unit surface area which results therefrom remains low and in practice has little consequence on the conditions of deposition of the microorganisms, whilst manufacture of the sieve is thereby simplified.

Preferably, having regard to the experiments carried out by the inventor, the said plurality of consecutive circles is formed by fourteen said circles.

Preferably, still for practical reasons of manufacture and quality of the results obtained:

- the said concentric circles on which the said holes in the said perforated wall are disposed are substantially equidistant; and/or
- the distance between two consecutive circles of the said concentric circles on which the said holes in the said perforated wall are disposed is between 1.8 and 2.2 mm.

According to other features preferred for the same reasons:

- the holes in the said perforated wall in the sieve all have substantially the same size; and/or
- the holes in the said perforated wall in the sieve all have a diameter of between 0.4 and 0.6 mm; and/or
- the number of holes per unit surface area of the said perforated wall is substantially uniform; and/or
- the number of holes per cm in the said perforated wall is between 20 and 30; and/or
- the number of holes in the said perforated wall is between 800 and 1200.

The disclosure of the invention will now be continued with a description of an example embodiment given below for illustration and nonlimitatively, with reference to the accompanying drawings.

IN THE DRAWINGS

FIG. 1 is a perspective view of an apparatus according to the invention.

FIG. 2 is a view of an apparatus according to FIG. 1 in elevation and section.

FIG. 3 is a plan view of the sieve included in this apparatus.

FIG. 4 is a graph showing the variation in the mean speed at which the air strikes the layer of growth media as a function of the volume of air sucked in.

DETAILED DESCRIPTION OF THE INVENTION

The apparatus 1 illustrated in FIG. 1 has a sampling head 2 and a body 3. The sampling head 2 has a sieve 4, an aerodynamic sleeve 5 on the end of which the sieve 4 is removably mounted, a deflector 6 disposed in the sleeve 5 so that there is an air suction duct 7 between the deflector and the sleeve, and a turbine 8 having a stator 9 fixed to the sleeve 5 and a rotor 10 for sucking air into the duct 7 and for discharging it through the side discharge orifice 9'.

The rotor 10 of the turbine 8 is driven by an electric motor 11, which partially enters the body 3.

The body 3 serves in general terms to hold the apparatus 1 and to control the motor 11. The body 3 has externally, opposite the head 2, feet 12 by means of which the apparatus 1 can be placed vertically. It also contains a base 13 having a threaded hole for fixing the apparatus 1, for example horizontally, to a support such as a conventional camera tripod, and a handle 14 for gripping the apparatus 1. The body 3 contains a set of electrical batteries 15, an electrical circuit 16 having a display 17 and a simplified keypad 18 disposed above the handle 14 as well as another electrical circuit 19, and a certain number of electrical conductors, not shown, serving to effect the necessary connections between the motor battery 15 and the circuits 16 and 19.

The sampling head 2 is designed to receive a receptacle 20 containing a layer of growth media 21 with a similar contour to that of the perforated wall 22 of the sieve 4, and to hold this receptacle in the illustrated position in which the layer of growth media is disposed opposite the perforated wall 22 and concentrically with it. The growth media is preferably a self supportive media such as agar, although other media may be used if supported on an appropriate support, such as a wicking paper or sponge.

The receptacle 20 is more precisely held by virtue of one or more notches (not illustrated) provided on the end of the aerodynamic sleeve 5. The notches retain the one or more lugs (not illustrated) formed on and projecting outwardly from the lateral wall of the receptacle 20. The fitting of the base of the receptacle 20 (the part of the receptacle opposite to the surface of the layer of growth media which faces the perforated wall 22) in the deflector 6 serving to close-off the latter. More details on the cooperation between the receptacle 20 and the sampling head 2 are given in the French patent application No 98-05166, to which reference can be made if desired.

It should be noted simply that the fact that the receptacle 20 and the sieve 4 are both mounted on the same support (the end of the sleeve 5) making it possible to have a very precise positioning of the sieve with respect to the receptacle, and that the surface of the layer of growth media 21 which is opposite the perforated wall 22 is preferably formed at the time of manufacture (when the layer of growth media 21 is poured) by a film tensioned over the end surface of the annular wall which surrounds the layer of growth media 21, so that the geometry of this surface is particularly precise and repetitive from one receptacle 20 to another.

Because of the conformation of the side wall of the receptacle 20 and that of the sieve 4, the duct 7 also exists all around the receptacle 20 so that, when the rotor 10 rotates, there is a suction of air at the periphery of the receptacle 20 and therefore a suction of external air which enters the apparatus 1 through the multitude of holes in the perforated wall 20, as shown by the arrows in FIG. 2.

Whereas the surface of the layer of growth media 21 which faces the wall 22 is flat (it may also be very slightly curved because the film delimiting this surface at the time of manufacture may adopt a small deflection when the growth media is poured), the wall 22 is curved in the direction in which it is concave on the side which faces the layer of growth media 21. Preferably, it is in a portion of a sphere, such as in the form of an arc, so that the separation between the wall 22 and the layer of growth media 21 increases from their periphery towards their center.

By virtue of this variable separation, the holes provided in the wall 22, which are particularly high in number as can be seen in FIGS. 1 and 3, are all capable of being useful, that is to say of each creating a flow of air coming to strike the layer of growth media 21 in the form of a jet which encounters the latter at a sufficiently high speed for any microorganism present in the flow of air to be fixed on the layer of growth media by impaction and sufficiently low for the microorganism to remain revivable.

As can be seen more particularly in FIG. 3, the holes in the perforated wall 22 are solely disposed in concentric circles as well as in six circular sectors delimited by the radii 23A to 23F, which are disposed at 60° to each other.

The holes in the first fourteen consecutive circles as from the center of each of the six sectors are disposed in a series of parallel chevrons whose apex is turned towards the center, so that there are six identical series of chevrons which are externally delimited respectively by the chevron formed by the radii 23A and 23B, by that formed by the radii 23B and 23C and so on.

As a result, for each series of chevrons, the apex of the one which is furthest towards the outside is situated on the hole which is exactly at the center of the perforated wall 22, the apex of the second chevron is on a hole in the second circle, and so on until the seventh and last chevron, whose apex is on the twelfth consecutive circle from the center.

From the fifteenth to the eighteenth and last circle, the number of holes remains the same as for the fourteenth circle, each of the holes in these circles being aligned on a radius, with a respective hole in the fourteenth circle.

As can be seen in FIG. 3 for the sector situated between the radii 23A and 23B, where all the alignments of holes have been depicted, there are channels between these alignments, going as far as the periphery of the wall 22, the number of the channels being higher as the periphery of this wall is approached.

When the rotor 10 is driven in rotation, the jets of air existing between the wall 22 and the layer of growth media 21 are disposed in the same way as the holes in this wall, and there therefore exist, between the alignments of air jets, paths (corresponding to the above mentioned channels) by virtue of which the air can be discharged without obstacle to the peripheral suction channel 7, so that coexistence between the air entering the apparatus in the form of jets and that discharging at the periphery is achieved with a minimum degree of mutual interference.

It will be observed that the concentric circles in which the holes in the wall 22 are substantially equidistant, and preferably this distance is around 2 mm. The holes in the wall 22 are preferably all substantially the same size, preferably a diameter of around 0.5 mm. The number of holes per unit surface area of the perforated wall is substantially uniform, preferably around 25 holes per $cm^2$, and that the total number of holes in the wall 22 is typically slightly less than 1000 holes.

Because the separation between the layer of growth media 21 and the perforated wall 22 has geometric characteristics which are repeated from one receptacle 20 to another, the air flow sucked in for each rotation of the rotor 10 remains the same and consequently the speed at which the air strikes the layer of growth media 21 remains the same for the same speed of rotation of the rotor, and the volume of air sucked in remains the same for the same number of rotations effected by the rotor.

FIG. 4 shows how the mean speed at which the layer of growth media 21 is struck by the air jets is varied according to the volume already sucked in, that is to say how the circuits 16 and 19 vary the speed of rotation of the motor 11 as a function of the number of rotations already effected by the latter.

At the start, the speed of rotation of the motor 11 is fixed so that the mean speed of the air through the holes in the wall 22 (the ratio between the total flow rate and the total surface area of the holes) is around 11.5 m/s and this speed is maintained constant until a volume of approximately 500 liters has been sucked in, and the speed of rotation of the motor is then increased so that the mean speed is 15 m/s and this speed of rotation is maintained until the whole of the sample, that is to say 1000 liters (1 $m^3$), has been sucked in.

This variation in the speed of impaction on the growth media as a function of the volume already sucked in reduces the risk that the microorganisms may not be retained by the layer of growth media because the latter undergoes a certain degree of drying as the sample is taken at each place where the growth media is struck by an air jet, the increase in speed compensating for the increase in hardness and the reduction in adhesion due to the drying.

In other variants which are not shown, the air suction rate (and therefore the mean speed at which the growth media is struck) is increased progressively rather than in stages or with more than two stages; the holes are distributed differently on the perforated wall 22, notably by providing a different number of concentric circles and radii delimiting sectors where the holes are distributed identically; and/or the increase in separation between the layer of growth media and the perforated wall is achieved differently, for example with a perforated wall which is flat and a layer of growth media which is concave on the side which faces the perforated wall.

Numerous other variants are possible according to circumstances, and it should be stated in this regard that the invention is not limited to the examples described and depicted.

What I claim:

1. A sampling apparatus for the microbiological analysis of air, comprising a sieve with a wall perforated with a multitude of holes, wherein the perforated wall of the sieve is in the form of a spherical cap, a sleeve for holding a removable receptacle containing a layer of growth media and which sleeve is capable of holding such receptacle in a predetermined position in relationship to the said perforated wall, a means for sucking air at the periphery of the said receptacle held in the said predetermined position, in order to cause air to enter the said apparatus, through the said holes and to strike be said layer of growth media, and wherein the said perforated wall of the sieve and the said layer of growth media in the receptacle are shaped so that their separation increases from their periphery to their center.

2. An apparatus according to claim 1, wherein the said perforated wall of the sieve is concave on the side which faces the said layer of growth media and the layer of growth media is substantially flat on the side which faces the perforated wall of the sieve.

3. An apparatus according to claim 1 wherein the said holes in the said perforated wall are substantially arranged in circles which are concentric and, for a plurality of said circles, consecutive as from the center, in a plurality of identical series of substantially parallel chevrons whose apex is turned towards the center, each said series of chevrons being delimited externally by a chevron formed by two radii and for each circle in the said plurality of circles, the nth circle from the center has sn holes, s being the number of identical series of chevrons.

4. An apparatus according to claim 1 wherein the holes in the said perforated wall of the sieve are all substantially the same size.

5. An apparatus according to claim 3 wherein the said plurality of identical series of chevrons is formed by six of said series.

6. An apparatus according to claim 3 wherein as from the (p+1)th consecutive circle from the center, each circle has the same number of holes as the pth circle and each of its holes is aligned, on a radius, with a respective hole of the pth circle, p being the number of circles in the said plurality of consecutive circles.

7. An apparatus according to claim 6 wherein the said plurality of consecutive circles is formed by fourteen said circles.

8. An apparatus according to claim 3 wherein the said concentric circles on which the said holes in the said perforated wall are disposed are substantially equidistant.

9. An apparatus according to claim 3 wherein the distance between two consecutive circles of the said concentric circles on which the said holes in the said perforated wall are disposed is between about 1.8 and about 2.2 mm.

10. An apparatus according to claim 1 wherein the holes in the said perforated wall of the sieve all have a diameter of between about 0.4 and about 0.6 mm.

11. An apparatus according to claim 1 wherein the number of holes per unit surface area of the said perforated wall is substantially uniform.

12. An apparatus according to claim 1 wherein the number of holes per $cm^2$ in the said perforated wall is between about 20 and about 30.

13. An apparatus according to claim 1 wherein the number of holes in the said perforated wall is between about 800 and about 1200.

14. An apparatus for sampling microorganisms from the air comprising a body and a sampling head, said sampling head having a sieve, said sieve mounted to a sleeve and containing a series of one or more holes, said holes are substantially arranged in circles which are concentric and for a plurality of said circles, consecutive as from the center, in a plurality of identical series of substantially parallel chevrons whose apex is turned toward the center, each said series of chevrons being delimited externally by a chevron formed of two radii, a deflector mounted in the sleeve so as to form an air duct between the deflector and the sleeve, a rotor having a turbine and a stator, said stator being fixed to a portion of the sleeve opposite the sieve and an air outlet in the stator, said head being removably attached to the body, said body having an electrical motor connected to the rotor so as to drive the turbine, one or more batteries for the motor, an electrical circuit to control the supply of power from the batteries to the motor, said head also containing a receptacle containing a layer of growth media, said receptacle being removably fixed within the sleeve of the head so as to be concentric with and precisely positioned relative to the sieve and wherein the said sieve and the said layer of growth media in the receptacle are shaped so that their separation increases from their periphery to their center.

15. An apparatus according to claim 14, wherein the said sieve is concave on the side which faces the said layer of growth media and the layer of growth media is substantially flat on the side which faces the side of the sieve.

16. An apparatus according to claim 14 wherein for each circle in the said plurality of circles, the nth circle from the center has sn holes, s being the number of identical series of chevrons.

17. An apparatus according to claim 14 wherein the said plurality of consecutive circles is formed by fourteen said circles.

18. An apparatus according to claim 14 wherein as from the (p+1)th consecutive circle from the center, each circle has the same number of holes as the pth circle and each of its holes is aligned, on a radius, with a respective hole of the pth circle, p being the number of circles in the said plurality of consecutive circles.

19. An apparatus according to claim 14 wherein the distance between two consecutive circles of the said concentric circles on which the said holes in the said perforated wall are disposed is between about 1.8 and about 2.2 mm and the holes in the said sieve are all substantially the same size.

20. An apparatus according to claim 14 wherein the holes in the said sieve all have a diameter of between about 0.4 and about 0.6 mm.

* * * * *